United States Patent
Chauhan et al.

(10) Patent No.: US 7,270,772 B2
(45) Date of Patent: Sep. 18, 2007

(54) BENZOPYRAN COLORANTS, METHOD OF MANUFACTURE, AND METHOD OF USE

(75) Inventors: Yogendrasinh B. Chauhan, Vadodara (IN); Adil Minoo Dhalla, Maharashtra (IN); Rahul R. Khanwelkar, Maharatra (IN); Krishnamoorthy Sivakumar, Bangalore (IN); Kiran Arunkumar Puthamane, Karnataka (IN)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/289,159

(22) Filed: Nov. 28, 2005

(65) Prior Publication Data

US 2007/0122746 A1   May 31, 2007

(51) Int. Cl.
*C09K 11/02* (2006.01)
*C07D 491/12* (2006.01)
(52) U.S. Cl. ............... 252/301.35; 546/48; 252/301.21
(58) Field of Classification Search ........... 252/301.35, 252/301.21; 546/48
See application file for complete search history.

(56) References Cited

U.S. PATENT DOCUMENTS 3,880,869 A * 4/1975 Scheuermann et al. ....... 546/51
5,470,502 A   11/1995 Hahn et al.
5,840,817 A   11/1998 Shim et al.

FOREIGN PATENT DOCUMENTS

EP      42090       12/1983

OTHER PUBLICATIONS

EP0042090; Publication Date Dec. 23, 1981; (translation of abstract only).

JP 06-299111; Publication Date Oct. 25, 1994 (translation of abstract only).

JP 06-316649; Publication Date Nov. 15, 1994 (translation of abstract only).

* cited by examiner

*Primary Examiner*—Charanjit S. Aulakh

(57) ABSTRACT

A compound of Formula (I)

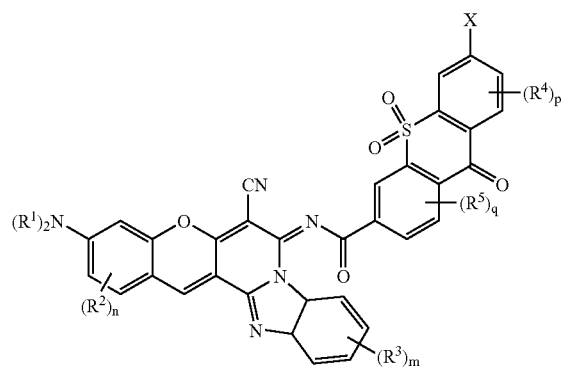

wherein X is hydrogen or a radical of Formula (II), $R^1$ independently at each occurrence is a $C_1$–$C_{20}$ aliphatic radical, a $C_3$–$C_{10}$ cycloaliphatic radical, or a $C_3$–$C_{10}$ aromatic radical; $R^2$, $R^3$, $R^4$ and $R^5$ are independently at each occurrence a halogen, a nitro group, a cyano group, a hydroxy group, a $C_1$–$C_{20}$ aliphatic radical, a $C_3$–$C_{20}$ cycloaliphatic radical, or a $C_6$–$C_{20}$ aromatic radical; and "n", "q", and "p" are each independently integers having a value of 0 to 3, and "m" is an integer having a value of 0 to 4.

17 Claims, No Drawings

BENZOPYRAN COLORANTS, METHOD OF MANUFACTURE, AND METHOD OF USE

BACKGROUND

This disclosure generally relates to benzopyran compounds. More particularly the disclosure relates to benzopyran colorants having high thermal stability.

A wide variety of colorants are known to be useful in coloring many different kinds of polymers. Colorants having high glass transition temperatures (Tg) for stability during processing, and good weatherability properties under a variety of conditions are in great demand in the coloration of thermoplastics. However, it is difficult to find colorants with these stability properties that also impart a desirable color and good color value to products.

Accordingly, there is a continuing need for new colorant compounds that have good chroma, good fluorescent intensity, and good weatherability and at the same time can also be processed at high temperatures.

BRIEF SUMMARY

Disclosed herein are compounds of Formula (I),

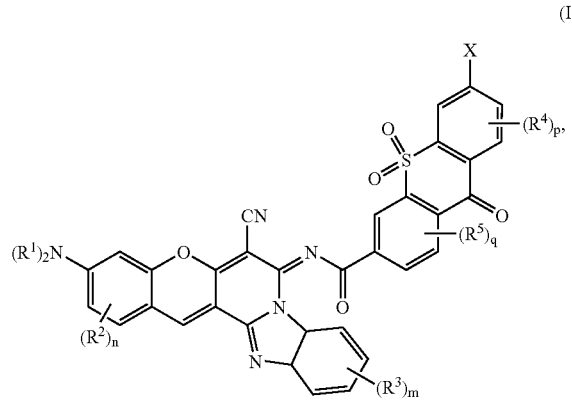

wherein X is hydrogen or a radical of Formula (II)

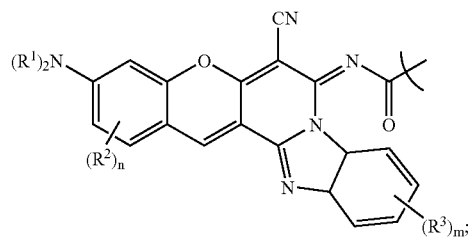

$R^1$ independently at each occurrence is a $C_1$–$C_{20}$ aliphatic radical, a $C_3$–$C_{10}$ cycloaliphatic radical, or a $C_3$–$C_{10}$ aromatic radical;

$R^2$, $R^3$, $R^4$ and $R^5$ are independently at each occurrence a halogen, a nitro group, a cyano group, a hydroxy group, a $C_1$–$C_{20}$ aliphatic radical, a $C_3$–$C_{20}$ cycloaliphatic radical, or a $C_6$–$C_{20}$ aromatic radical;

"n", "q", and "p" are each independently integers having a value of 0 to 3, and "m" is an integer having a value of 0 to 4.

In another embodiment a process for producing the compounds of Formula (I) comprises reacting a compound of Formula (III) with a compound of Formula (IV) in the presence of a first catalyst and a first solvent

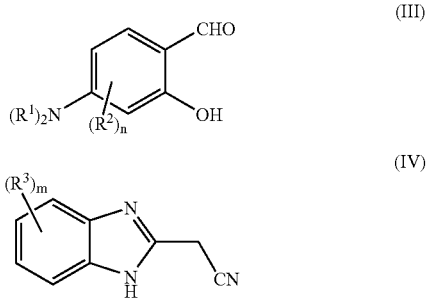

to provide a compound of Formula (V)

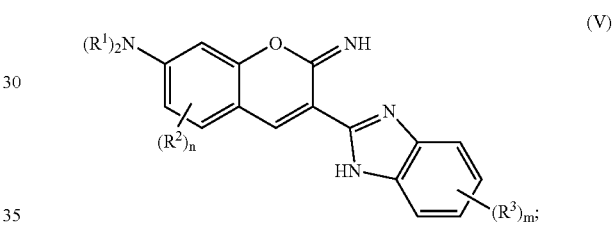

reacting the compound of Formula (V) with malononitrile in the presence of a second solvent to provide a compound of Formula (VI)

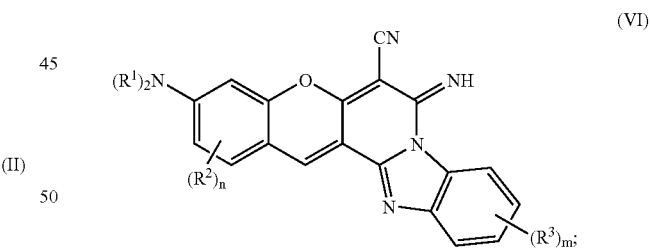

and reacting the compound of Formula (VI) with a compound of Formula (VII) or Formula (VIII)

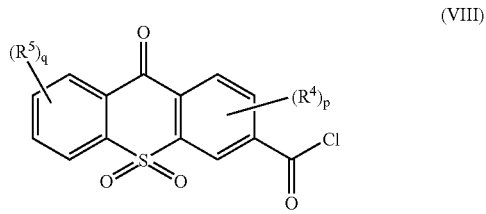

-continued

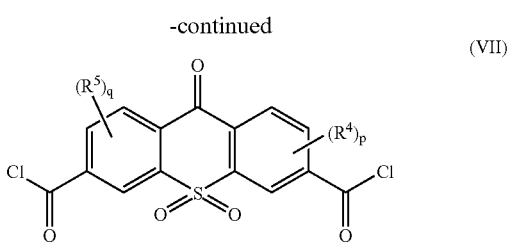

(VII)

in the presence of a second catalyst and a third solvent to provide a compound of Formula (I), as described above, wherein X, $R^1$, $R^2$, $R^3$, $R^4$, $R^5$, "n", "q", "p" and "m" have the same meaning as defined above.

In one embodiment a composition comprises a polymer and a compound of Formula (I) as described above.

In another embodiment, an article comprises the above-described polymer composition.

The disclosure may be understood more readily by reference to the following detailed description of the various features of the disclosure and the examples included therein.

DETAILED DESCRIPTION

Disclosed herein are benzopyran compounds and methods for preparing these compounds. These compounds are useful as colorants in the preparation of colored polymers, especially in the preparation of thermoplastic colored polymers. The compounds are stable at high temperatures, and have good weatherability, and thus can be used in polymer compositions for forming a variety of articles.

The singular forms "a", "an" and "the" include plural referents unless the context clearly dictates otherwise. All ranges disclosed herein are inclusive of the recited endpoint and independently combinable (for example ranges of "up to 25 weight (wt.) percent, with 5 wt. percent to 20 wt. percent desired," is inclusive of the endpoints and all intermediate values of the ranges of "5 wt. percent to 25 wt. percent").

The modifier "about" used in connection with a quantity is inclusive of the stated value and has the meaning dictated by the context (for example, includes the degree of error associated with measurement of the particular quantity).

Compounds are described using standard nomenclature. For example, any position not substituted by any indicated group is understood to have its valency filled by a bond as indicated, or a hydrogen atom. A dash ("—") that is not between two letters or symbols is used to indicate a point of attachment for a substituent. For example, —CHO is attached through carbon of the carbonyl group.

Unless otherwise specified, the term "cycloaliphatic functionality" designates cyclic aliphatic functionalities having a valence of at least one, and comprising an array of atoms that is cyclic but that is not aromatic. The cycloaliphatic functionality may include heteroatoms such as nitrogen, sulfur, selenium, silicon and oxygen, or may be composed exclusively of carbon and hydrogen. A "cycloaliphatic functionality" may be linked via the cyclic group or via another group on the cyclic group. For example, a cyclohexylmethyl group ($C_6H_{11}CH_2$—) is a cycloaliphatic functionality which comprises a cyclohexyl ring (the array of atoms which is cyclic but which is not aromatic) and a methylene group (the noncyclic component). A "cycloaliphatic moiety" may further be unsubstituted or substituted, i.e., comprising one or more noncyclic components, including functional groups such as alkyl groups, alkenyl groups, alkynyl groups, haloalkyl groups, halogen(s), conjugated dienyl groups, alcohol groups, ether groups, carboxylic acid groups, acyl groups (for example carboxylic acid derivatives such as esters and amides), amine groups and nitro groups. For example, the 4-methylcyclopent-1-yl group is a $C_6$ cycloaliphatic functionality comprising a methyl group, wherein the methyl group is a functional group which is an alkyl group. Similarly, the 2-nitrocyclobut-1-yl group is a $C_4$ cycloaliphatic functionality comprising a nitro group, wherein the nitro group is a functional group. Exemplary cycloaliphatic functionalities include cyclopropyl, cyclobutyl, 1,1,4,4-tetramethylcyclobutyl, piperidinyl, 2,2,6,6-tetramethylpiperydinyl, cyclohexyl, and cyclopentyl.

As used herein, the term "aromatic functionality" refers to an array of atoms having a valence of at least one, and comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic functionality" includes but is not limited to phenyl, pyridyl, furanyl, thienyl, naphthyl, phenylene, and biphenyl functionalities. The aromatic functionality may also include nonaromatic components. For example, a benzyl group is an aromatic functionality that comprises a phenyl ring (the aromatic group) and a methylene group (the nonaromatic component). Similarly a tetrahydronaphthyl functionality is an aromatic functionality comprising an aromatic group ($C_6H_3$) fused to a nonaromatic component —$(CH_2)_4$—. An "aromatic functionality" may further be unsubstituted or substituted with a wide range of functional groups such as alkyl groups, haloalkyl groups, haloaromatic groups, halogens, alcohol groups, ether groups, carboxylic acid groups, acyl groups (for example carboxylic acid derivatives such as esters and amides), amine groups and nitro groups. For example, the 4-methylphenyl functionality is a $C_7$ aromatic functionality comprising a methyl group, wherein the methyl group is a functional group which is an alkyl group. Similarly, the 2-nitrophenyl group is a $C_6$ aromatic functionality comprising a nitro group, wherein the nitro group is a functional group. Exemplary aromatic functionalities include, but are not limited to phenyl, 4-trifluoromethylphenyl, 4-chloromethylphen-1-yl, 3-trichloromethylphen-1-yl (3-$CCl_3$Ph—), 4-(3-bromoprop-1-yl) phen-1-yl (4-$BrCH_2CH_2CH_2$Ph—), 4-aminophen-1-yl (4-$H_2$NPh—), 4-hydroxymethylphen-1-yl (4-$HOCH_2$Ph—), 4-methylthiophen-1-yl (4-$CH_3$SPh—), 3-methoxyphen-1-yl, 2-nitromethylphen-1-yl (2-$NO_2CH_2$Ph), and naphthyl.

As used herein the term "aliphatic functionality" refers to an organic functionality having at least one carbon, a valence of at least one consisting of a linear or branched array of atoms that is not cyclic. The array of atoms comprising the aliphatic functionality may include heteroatoms such as nitrogen, sulfur, silicon, selenium and oxygen or may be composed exclusively of carbon and hydrogen. An "aliphatic functionality" may be unsubstituted or substituted with a wide range of functional groups such as alkyl groups, haloalkyl groups, halogens, alcohol groups, ether groups, carboxylic acid groups, acyl groups (for example carboxylic acid derivatives such as esters and amides), amine groups and nitro groups. For example, the 4-methylpent-1-yl is a $C_6$ aliphatic functionality comprising a methyl group, wherein the methyl group is a functional group which is an alkyl group. Similarly, the 4-nitrobut-1-yl group is a $C_4$ aliphatic functionality comprising a nitro group, wherein the nitro group is a functional group. Exemplary aliphatic functionalities include, but are not limited to methyl, ethyl, propyl, isopropyl, butyl, isobutyl, pentyl, isopentyl, trifluoromethyl, bromodifluoromethyl, chlorodifluoromethyl, chloromethyl, trichloromethyl, bromoethyl, 2-hexyl, hexamethylene, hydroxymethyl (i.e., —CH$_2$OH), mercaptomethyl (—CH$_2$SH), methylthio (—SCH$_3$), methylthiomethyl (—CH$_2$SCH$_3$), methoxy, methoxycarbonyl (CH$_3$OCO—), nitromethyl (—CH$_2$NO$_2$) and thiocarbonyl.

Halogen as used herein includes fluorine, chlorine, bromine, and iodine.

Disclosed herein are dihydroxy aromatic compounds of Formula (I),

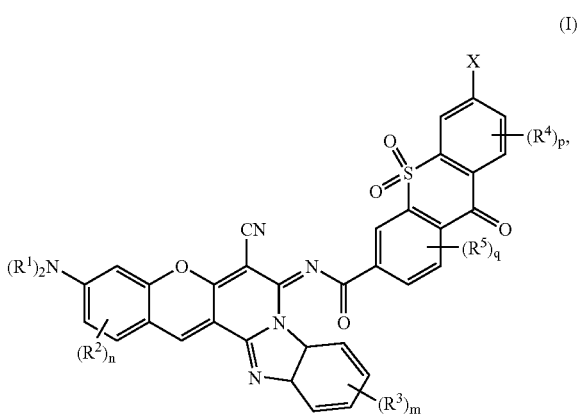

(I)

wherein X is hydrogen or a radical of Formula (II)

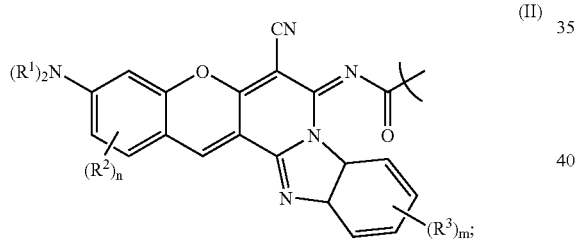

(II)

R$^1$ independently at each occurrence is a C$_1$–C$_{20}$ aliphatic radical, a C$_3$–C$_{10}$ cycloaliphatic radical, or a C$_3$–C$_{10}$ aromatic radical; R$^2$, R$^3$, R$^4$ and R$^5$ are independently at each occurrence a halogen, a nitro group, a cyano group, a hydroxy group, a C$_1$–C$_{20}$ aliphatic radical, a C$_3$–C$_{20}$ cycloaliphatic radical, or a C$_6$–C$_{20}$ aromatic radical; "n", "q", and "p" are each independently integers having a value of 0 to 3, and "m" is an integer having a value of 0 to 4.

In a specific embodiment, R$^1$ independently at each occurrence is a C$_1$–C$_{10}$ aliphatic radical, a C$_3$–C$_{10}$ cycloaliphatic radical, or a C$_6$–C$_{10}$ aromatic radical. In another specific embodiment, each R$^1$ is the same unsubstituted C$_1$–C$_6$ aliphatic radical.

In another specific embodiment, R$^2$, R$^3$, R$^4$ and R$^5$ are independently at each occurrence a halogen, a nitro group, or a cyano group, and "n", "q", "m" and "p" are each independently integers having a value of 0 to 2, specifically 0 to 1.

In still another specific embodiment, R$^2$, R$^3$, R$^4$ and R$^5$ are independently at each occurrence a halogen, a nitro group, or a cyano group, "n" and "q" are each independently integers having a value of 0 to 2, specifically 0 to 1, "m" is an integer having a value of 0 to 2, specifically 0 to 1, and "p" is an integer having a value of 0 to 1, specifically 0.

In another specific embodiment, each R$^1$ is the same unsubstituted C$_1$–C$_6$ aliphatic radical, R$^2$ and R$^3$ are independently at each occurrence a halogen, a nitro group, or a cyano group; "n" and "q" are each 0 or 1, "m" and "p" are each zero, and X is hydrogen or a radical of Formula (II).

In one embodiment the benzopyran compound comprises a compound of Formula (IX)

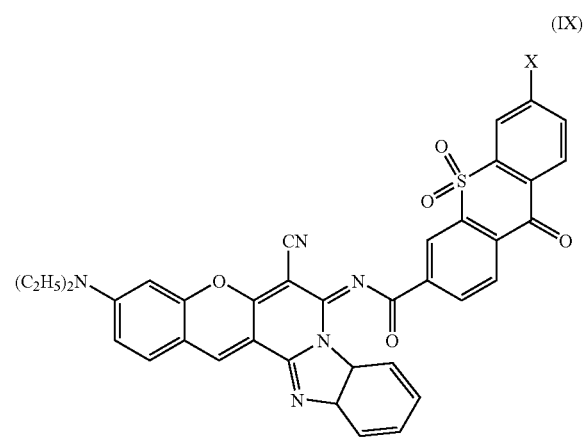

(IX)

wherein X is hydrogen or a radical of Formula (II). In a specific embodiment, X in Formula (IX) is hydrogen.

One process for making the benzopyran compound of Formula (I) is as follows. A compound of Formula (III) is reacted with a compound of Formula (IV)

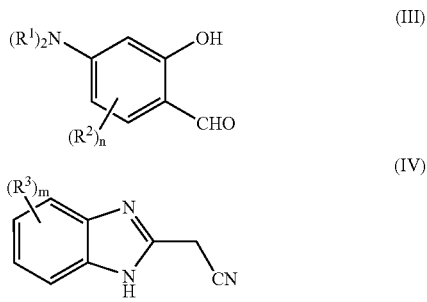

(III)

(IV)

in the presence of a first catalyst and a first solvent to provide a compound of Formula

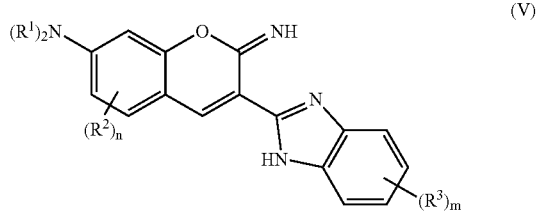

(V)

wherein R$^1$, R$^2$, R$^3$, R$^4$, R$^5$, "n" and "m" are defined as above.

Suitable compounds of Formula (III) include, but are not limited to, 4-diethylamino salicylaldehyde, 5-halo-4-diethylamino salicylaldehyde, 5-cyano-4-diethylamino salicylaldehyde and 5-nitro-4-diethylamino salicylaldehyde.

Suitable compounds of Formula (IV) include, but are not limited to, 2-benzimidazolyl acetonitrile, 6-nitro-2-benzimidazolyl acetonitrile, 6-cyano-2-benzimidazolyl acetonitrile and 6-halo-2-benzimidazolyl acetonitrile.

The amount of the compound of Formula (IV) employed in the reaction can be about 0.75 to about 4.0 moles per mole of compound of Formula (III) employed. Within this range the amount may be greater than or equal to 1.0 mole, or, more specifically, greater than or equal to about 1.5 moles. Also within this range the amount may be less than or equal to about 3.0 moles, or, more specifically less than or equal to about 2.5 moles.

Suitable first catalysts may be selected from the group consisting of an acid or a base. Exemplary bases include, but are not limited to, piperidine, ethyldiisopropylamine, triethylamine, pyridine, pyrrolidone, morpholine, sodium carbonate, potassium carbonate, sodium methylate and potassium methylate. Exemplary acids include, but are not limited, to p-toluenesulfonic acid, benzenesulfonic acid, phosphoric acid, tetrafluoroboric acid and hydrochloric acid.

The amount of first catalyst employed in the reaction can be about 0.01 moles to about 0.2 moles per mole of compound of Formula (III) employed. Within this range the amount may be greater than or equal to about 0.02 moles, or, more specifically greater than or equal to about 0.03 moles. Also within this range the amount may be less than or equal to about 0.1 moles, or, more specifically less than or equal to about 0.05 moles.

Specific examples of suitable first solvents that can be employed in the reaction of the compound of Formula (III) with the compound of Formula (IV) to produce the compound of Formula (V) include, but are not limited to ethanol, methanol, isopropanol, n-propanol, n-butanol, isobutanol, ethylene glycol, ethylene glycol monomethyl ether, chlorobenzene, dichlorobenzene, trichlorobenzene, dimethyl formamide, N-methylpyrrolidone, or a combination comprising at least one of the foregoing solvents. In one embodiment the solvent is ethanol, methanol, or a combination of ethanol and methanol. In certain embodiments the amount of solvent employed in the reaction of the compound of Formula (III) with the compound of Formula (IV) can be about 200 liters to about 500 liters per mole of compound of Formula (III). Within this range the amount may be greater than or equal to about 220 liters, or, more specifically, greater than or equal to about 240 liters. Also within this range the amount may be less than or equal to about 360 liters, or, more specifically less than or equal to about 320 liters.

The temperature at which the reaction of the compound of Formula (III) with the compound of Formula (IV) takes place can be about 20° C. to about 40° C. Within this range the temperature may be greater than or equal to about 25° C., or, more specifically, greater than or equal to about 28° C. Also within this range the temperature may be less than or equal to about 35° C., or, more specifically, less than or equal to about 30° C. The time taken for the reaction of the compound of Formula (III) with the compound of Formula (IV) can be about 15 hours to about 30 hours. Within this range the time may be greater than or equal to about 20 hours, or, more specifically, greater than or equal to about 22 hours. Also within this range the time may be less than or equal to about 28 hours, or, more specifically, less than or equal to about 25 hours.

The compound of Formula (V) is then reacted with malononitrile (NC—CH$_2$—CN) in the presence of a second solvent to provide a compound of Formula (VI)

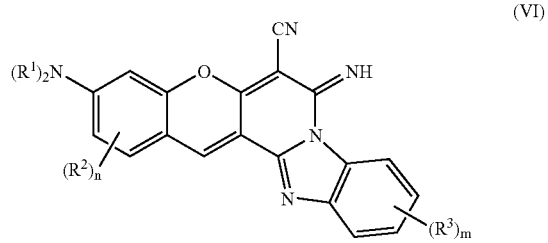

wherein $R^1$, $R^2$, $R^3$, "n" and "m" have the meaning as defined above. The amount of malononitrile employed in the reaction can be about 0.3 moles to 1.0 mole per mole of compound of Formula (V). Within this range the amount may be greater than or equal to about 0.4 moles, or, more specifically, greater than or equal to about 0.6 moles. Also within this range the amount may be less than or equal to about 0.9 moles, or, more specifically, less than or equal to about 0.8 moles.

Specific examples of suitable second solvents include, but are not limited to, 2-methoxyethanol, dimethylformamide, dimethylsulfoxide, dimethylacetamide, tetrahydrofuran, toluene, xylene, chlorobenzene, dichlorobenzene, trichlorobenzene and combinations of the foregoing. The amount of solvent employed in the reaction of malononitrile with the compound of Formula (V) comprises about 200 milliliters to about 400 milliliters per mole of the compound of Formula (V). Within this range the amount may be greater than or equal to about 220 milliliters, or, more specifically, greater than or equal to about 240 milliliters per mole of the compound of Formula (V). Also within this range the amount may be less than or equal to about 300 milliliters, or, more specifically, less than or equal to about 280 liters per mole of the compound of Formula (V).

The temperature of the reaction of malononitrile with a compound of Formula (V) can be about 100° C. to about 160° C. Within this range the temperature may be greater than or equal to about 110° C., or, more specifically, greater than or equal to about 120° C. Also within this range the temperature may be less than or equal to about 150° C., or, more specifically, less than or equal to about 140° C. The time for the reaction of malononitrile with a compound of Formula (V) can be about 5 hours to about 10 hours. Within this range the time may be greater than or equal to about 6 or, more specifically, greater than or equal to about 7 hours. Also within this range the time may be less than or equal to about 9 hours, or, more specifically, less than or equal to about 8 hours.

The compound of Formula (VI) is then reacted with a compound of Formula (VII) or Formula (VIII)

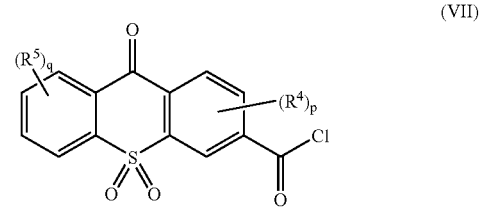

-continued

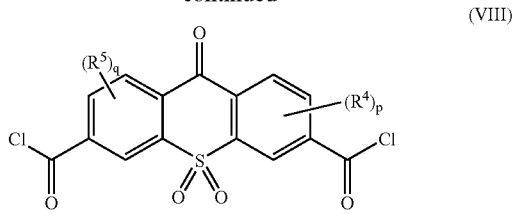

(VIII)

in the presence of a second catalyst and a third solvent to provide a compound of Formula (I), wherein $R^4$, $R^5$, "p" and "q" are as described above.

The amount of the compound of Formula (VI) employed in the reaction can be about 0.80 moles to about 1.30 moles per mole of the compound of Formula (VII). Within this range the amount may be greater than or equal to about 0.90 moles, or, more specifically, greater than or equal to about 1.10 moles. Also within this range the amount may be less than or equal to about 1.25 moles, or, more specifically, less than or equal to about 1.20 moles.

The amount of the compound of Formula (VI) employed in the reaction can be about 1.6 moles to about 2.6 moles per mole of the compound of Formula (VIII). Within this range the amount may be greater than or equal to about 1.8 moles, or, more specifically, greater than or equal to about 2.0 moles. Also within this range the amount may be less than or equal to about 2.4 moles, or, more specifically, less than or equal to about 2.2 moles.

Suitable second catalysts include but are not limited to bases such as, alkali metal carbonates, for example sodium carbonate and potassium carbonate, alkali metal acetates, for example sodium acetate and potassium acetate, and organic amines, for example, triethylamine, piperidine, ethyldiisopropylamine, pyridine, pyrrolidone, morpholine and pyridine.

The amount of second catalyst employed in the reaction can be about 0.5 moles to about 1.5 moles per mole of the compound of Formula (VI) employed. Within this range the amount may be greater than or equal to about 0.8 moles, or, more specifically greater than or equal to 1.0 mole. Also within this range the amount may be less than or equal to about 1.4 moles, or, more specifically less than or equal to about 1.2 moles.

Specific examples of a suitable third solvent that may be employed include, but are not limited to, benzene, toluene, xylene, 1,2-dichloroethane, chlorobenzene, dichlorobenzene, glycol ethers, dioxane, and tetrahydrofuran. The amount of third solvent employed in the reaction of compound having the compound of Formula (VI) with a compound of Formula (VII) or Formula (VIII) comprises about 500 milliliters to about 1000 milliliters per mole of the compound of Formula (VI). Within this range the amount may be greater than or equal to about 600 milliliters liters, or, more specifically, greater than or equal to about 700 milliliters per mole of compound of Formula (VI). Also within this range the amount may be less than or equal to about 900 milliliters, or, more specifically, less than or equal to about 800 milliliters per mole of compound of Formula (VI).

In certain embodiments the second catalyst may be used as the third solvent. In particular pyridine, piperidine, ethyldiisopropylamine, triethylamine, pyridine, pyrrolidone, and morpholine can be used both as the second catalyst and the third solvent. The amount of second catalyst employed when the catalyst also acts as a solvent in the reaction, can be 10 moles to about 70 moles per mole of the compound of Formula (VI) employed. Within this range the amount may be greater than or equal to about 20 moles, or, more specifically greater than or equal to about 30 moles. Also within this range the amount may be less than or equal to about 45 moles, or, more specifically less than or equal to about 40 moles.

The temperature of the reaction of the compound of Formula (VI) with the compound of Formula (VII) or Formula (VIII) can be about 40° C. to about 120° C. Within this range the temperature may be greater than or equal to about 50° C., or, more specifically, greater than or equal to about 60° C. Also within this range the temperature may be less than or equal to about 115° C., or, more specifically, less than or equal to about 90° C. The time for the reaction of the compound of Formula (VI) with the compound of Formula (VII) or Formula (VIII) can be about 1 hour to about 10 hours. Within this range the time may be greater than or equal to about 2 hours or, more specifically, greater than or equal to about 4 hours. Also within this range the time may be less than or equal to about 8 hours, or, more specifically, less than or equal to about 6 hours.

The compounds of Formula (VII) and Formula (VIII) may be prepared by reacting the corresponding acid compounds of Formula (IX) and Formula (X) respectively,

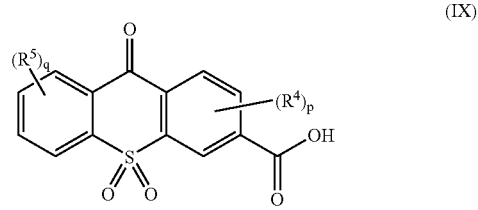

(IX)

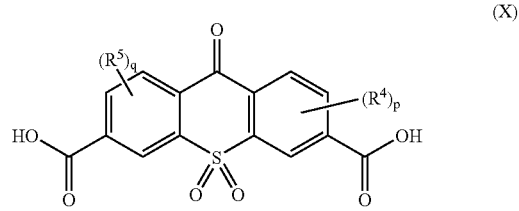

(X)

with a halogenating agent to provide the corresponding acid halide, wherein $R^4$, $R^5$, "p" and "q" have the same meaning as defined above. Typically the acid chlorides are prepared by reacting the corresponding carboxylic acid with halogenating agent such as phosphorous trichloride, phosphorous pentachloride, phosphorous oxy chloride, carbonyl chloride, thionyl chloride, oxalyl chloride or sulfuryl chloride. These reactions can take place either by using excess halogenating agents as the solvent or using the halogenating agent in the presence of a solvent including but not limited to, ethylene dichloride, methylene dichloride, toluene, dimethyl formamide, dimethylacetamide, dimethyl sulfoxide, toluene or xylene. The reaction is generally carried out at the reflux temperature of the reaction mixture. Once the reaction is complete, excess halogenating agent is distilled out to get the corresponding acid chloride. The acid chlorides may also be prepared by methods known to one skilled in the art.

In one embodiment a composition comprises a compound of Formula (I) as described above and another component that is different from the compound of Formula (I). As previously discussed, one of the end uses of the compounds of Formula (I) is use in the coloration of polymers, especially thermoplastic polymers, for example, polycarbonates, polyesters, polyimides and others. A specific embodiment therefore comprises a compound of Formula (I) in combination with a thermoplastic polymer.

The compound of Formula (I) is added to the polymer in an amount sufficient to be detected visually or by an analytical method as discussed below. In one embodiment, the compound of Formula (I) may be present in the polymer in an amount equal to about 0.05 percent by weight to about 20 percent by weight, based on the weight of the polymer. In another embodiment, the compound of Formula (I) may be present in the polymer in an amount of less than or equal to about 5.0 percent by weight, based on the weight of the polymer. In one embodiment, the compound of Formula (I) may be present in the polymer in an amount of about 0.2 percent by weight based on the weight of the polymer. In one embodiment, the compound of Formula (I) may be present in the polymer in an amount equal to about 1 part per billion (ppb). In an exemplary embodiment the amount is about 1 parts per million (ppm) to about 0.2 wt. percent. When used as a colorant, the concentration of the compound should be sufficient to allow a color change in the polymer and provide the required color value that would be detectable by the human eye. This implies that if the detector is the human eye, the emission is sufficient to be visually detectable.

A method for making a colored polymer comprises combining a polymer and a composition comprising the compound of Formula (I), to provide a colored polymer. Mixtures of compounds of Formula (I) can be used. Other components in the composition comprising the compound of Formula (I) may be, for example, pigments, other colorants, other additives described below, and the like. As used herein, "combining" and a "combination" includes blends, alloys, mixtures, reaction products, and the like. In one specific embodiment the amount of compound of Formula (I) is about 1 part per million (ppm) to about 0.2 wt. percent of the weight of the polymer.

In addition to the polymer and the compound of Formula (I), the polymer compositions disclosed herein may optionally include various additives ordinarily incorporated in resin compositions of this type. Such additives may include antioxidants, heat stabilizers, flame retardants, ultraviolet (UV) stabilizers, anti-static agents (tetra alkylammonium benzene sulfonate salts, tetra alkylphosphonium benzene sulfonate salts, and the like), mold releasing agents (pentaerythritol tetrastearate; glycerol monostearate, and the like). A combination comprising at least one of the foregoing can be used. For example, the polymer composition can comprise a heat stabilizer in an amount of about 0.01 weight percent to about 0.1 weight percent; an antistatic agent in an amount of about 0.01 weight percent to about 1 weight percent; and a mold releasing agent in an amount of about 0.1 weight percent to about 1 weight percent; each based upon the total weight of the polymer.

Some possible antioxidants include, for example, organophosphites, e.g., tris(nonyl-phenyl)phosphite, tris(2,4-di-t-butylphenyl)phosphite, bis(2,4-di-t-butylphenyl)pentaerythritol diphosphite, distearyl pentaerythritol diphosphite and the like; alkylated monophenols, polyphenols and alkylated reaction products of polyphenols with dienes, such as, for example, tetrakis[methylene(3,5-di-tertiary-butyl-4-hydroxyhydrocinnamate)]methane, 3,5-di-tertiary-butyl-4-hydroxyhydrocinnamate octadecyl, 2,4-di-tertiary-butylphenyl phosphite, and the like; butylated reaction products of para-cresol and dicyclopentadiene; alkylated hydroquinones; hydroxylated thiodiphenyl ethers; alkylidene-bisphenols; benzyl compounds; esters of beta-(3,5-di-tertiary-butyl-4-hydroxyphenyl)-propionic acid with monohydric or polyhydric alcohols; esters of beta-(5-tertiary-butyl-4-hydroxy-3-methylphenyl)-propionic acid with monohydric or polyhydric alcohols; esters of thioalkyl or thioaryl compounds, such as, for example, distearylthiopropionate, dilaurylthiopropionate, ditridecylthiodipropionate, and the like; amides of beta-(3,5-di-tertiary-butyl-4-hydroxyphenyl)-propionic acid; and the like. A combination comprising at least one of the foregoing can be used.

Other potential additives which may be employed comprise: stabilizers such as light and thermal stabilizers (e.g., acidic phosphorous-based compounds); hindered phenols; zinc oxide, zinc sulfide particles, or combination thereof; lubricants (mineral oil, and the like), plasticizers, colorants; among others, as well as a combination comprising at least one of the foregoing additives.

In order to aid in the processing of the colored polymer, particularly when the polymer is polycarbonate, catalyst(s) may also be employed, namely in the extruder or other mixing device. The catalyst typically assists in controlling the viscosity of the resulting material. Possible catalysts include hydroxides, such as tetraalkylammonium hydroxide, tetraalkylphosphonium hydroxide, and the like, specifically diethyldimethylammonium hydroxide and tetrabutylphosphonium hydroxide. The catalyst(s) can be employed alone or in combination with quenchers such as acids, such as phosphoric acid, and the like. Additionally, water may be injected into the polymer melt during compounding and removed as water vapor through a vent to remove residual volatile compounds.

The colored polymers disclosed herein are produced by using a reaction vessel capable of adequately mixing various precursors, such as a single or twin screw extruder, kneader, blender, or the like.

Methods for incorporating the compound of Formula (I) and any other optional additives into the polymer include, for example, coating, admixing, blending, or copolymerisation. The compound of Formula (I) can be incorporated into the polymer such that it is uniformly dispersed throughout the polymer or such that it is dispersed in a portion of the polymer. In one exemplary embodiment, the compound of Formula (I) is uniformly dispersed throughout the polymer. The compound of Formula (I) can be incorporated into the polymer in the polymer manufacturing stage, during the polymer compounding step, during polymer processing into articles, or combinations thereof. In one embodiment, the compound of Formula (I) may be introduced using a concentrate (i.e., master-batch) either during the polymer compounding stage or during the article forming, alone or with other optional additives.

For example, the polymer precursors for the polymer can be premixed with the compound of Formula (I) (e.g., in a pellet, powder, and/or liquid form) and simultaneously fed through a hopper into the extruder, or the compound of Formula (I) can be optionally added in the feed throat or through an alternate injection port of the injection molding machine or other molding. In one exemplary embodiment, the compound of Formula (I) may be homogenously distributed unless it is placed in a carrier that is not miscible with the polymer.

In another embodiment, the compound of Formula (I) is incorporated into the polymer by admixing, blending, compounding, or copolymerisation. In one exemplary embodiment, the compound of Formula (I) is incorporated into the polymer by forming a dry blend of the compound of Formula (I) with the polymer and compounding the resultant mixture.

In another embodiment, the compound of Formula (I) may be incorporated into the polymer by adding the compound of Formula (I) to the melt during compounding. Such additions may be made via a side feeder, for example. Alternatively, the compound of Formula (I) can be formulated with a small amount of the polymer (or another polymer), optionally with other additive(s) in the form of a concentrate and added to the polymer before or during processing of the polymer. In a specific embodiment, the polymer compositions are processed by compounding the polymer with any additive(s) using a twin-screw extruder, and adding the compound of Formula (I) in the form of a concentrate, optionally with other additives, to the melt via a side feeder.

When the polymer precursors are employed, the extruder is maintained at a sufficiently high temperature to melt the polymer precursors without causing decomposition thereof. For polycarbonate, for example, temperatures of about 220° C. to about 360° C. may be used in one embodiment. In another embodiment temperatures of about 260° C. to about 320° C. may be utilized. Similarly, the residence time in the extruder is typically controlled to minimize decomposition. Residence times of up to about 2 minutes or more may be employed, with up to about 1.5 minutes used in one embodiment, and up to about 1 minute used in another exemplary embodiment. Prior to extrusion into the desired form (typically pellets, sheet, web, or the like), the resulting mixture can optionally be filtered, such as by melt filtering and/or the use of a screen pack, or the like, to remove undesirable contaminants or decomposition products.

The colored polymer compositions may be used for any application in which the physical and chemical properties of the material are desired. In certain embodiments the colored polymers may be used in applications including packaging material (and especially drug packaging), automotive parts, telecommunication accessories (for example, cell phone covers), computers and consumer electronics, construction materials, medical devices, eyewear products, secure documents including passports and ID cards, credit cards, films and sheets (including those used in display applications), and the like. The colorants may also be used to make compositions for tagging and authenticating data storage media substrates that are currently unknown and/or unavailable to unauthorized manufacturers, sellers, and/or users of data storage media as they fluoresce at a particular wavelength when exposed to ultraviolet radiation.

A further understanding of the techniques described above can be obtained by reference to certain specific examples that are provided herein for purposes of illustration only, and are not intended to be limiting.

EXAMPLES

Proton NMR spectra for all the starting materials and products described herein were measured using a 300 megahertz Bruker NMR spectrometer using deuterated chloroform or $Cd_6$-dimethylsulfoxide as a solvent. Compounds were further characterized by a liquid chromatograph-mass spectrometer (LC-MS) system, comprising a liquid chromatograph and a Quattro Ultima Pt mass spectrometer. Absorbance was measured using Lambda 900 UV-Visible spectrometer.

The thermal stability for the benzopyran colorant was measured using a TGA 2950 from TA Instruments in air, with a ramp time of 10° C./min.

Example 1

This example provides a method for the preparation of 9,10,10-trioxo-9,10-dihydro-10,16-thioxanthene-3-carboxylic acid (6-cyano-9-diethylamino-7-oxa-4b,13-diazaindeno[2,1-a]anthracen-5-ylidene)-amide (Formula (I)).

Preparation of 7-N,N-diethylamino-3-benzimidazolyl-2-iminocoumarin. (Formula (V)).

2-Cyanomethyl benzimidazole (16.64 grams (g)), 4-diethylamino-salicyladehyde (17.74 g) and piperidine (3.6 milliliters (ml)) were stirred at room temperature in methanol (280 ml) for 24 hours (hrs). After about 24 hrs, a pale yellow colored solid separated out. The precipitated solid was filtered, washed with methanol (100 ml) and dried. The product was obtained in a yield of 27.5 g. This product was used in the next step without further purification.

Preparation of 9-diethylamino-5-imino-5H-7-oxa-4b,13-diazaindeno [2,1-a]anthracene-6-carbonitrile (Formula (VI))

7-N,N-Diethylamino-3-benzimidazolyl-2-imino coumarin (25 g) and malononitrile (5.5 g) and 250 ml of ethyl cellosolve were added to a 500 ml round bottom flask equipped with an oil-bath and the contents of the flask were refluxed for about 6 hrs maintaining the temperature 180° C. The reaction mixture was then cooled to 5° C. The solid that separated out was filtered. The solid was first washed with 50 ml of ethanol and then with 50 ml of hexane.

Preparation of 9-oxo-9H-thioxanthene-10,10-dioxide-3-carboxylic acid chloride (Formula (VII))

9-Oxo-9H-thioxanthene-10,10-dioxide-3-carboxylic acid (5 g) was refluxed in thionyl chloride (30 ml) for 12 hrs. The thionyl chloride was distilled out. The solid, which is left behind, is the required acid chloride that is directly used for the next reaction.

Preparation of 9,10,10-Trioxo-9,10-dihydro-1016-thioxanthene-3-carboxylic acid (6-cyano-9-diethylamino-7-oxa-4b,13-diaza-indeno[2,1-a]anthracen-5-ylidene)-amide (Formula (I))

9-Diethylamino-5-imino-5H-7-oxa-4b,13-diazaindeno[2,1-a]-anthracene-6-carbonitrile (1.52 g) is added to a three neck round bottom flask. Pyridine (20 ml) was added to the flask and the mixture was heated to about 90° C. At this temperature, 9-oxo-9H-thioxanthene-10,10-dioxide-3-carboxylic acid chloride (2.5 g) was added to the reaction mixture. The reaction mixture was maintained at this temperature for about 3 hrs. The reaction mixture was then poured on ice. The solid that separated out was filtered and washed with water and hexane. The product is purified by refluxing in a mixture of ethyl acetate and hexane (70:30 ratio volume by volume). The product was obtained in a yield of 2.5 g. Proton NMR of the product showed peaks at δ 1.4(t, 2X—N—CH$_2$—CH$_3$), 3.8(q, 2X—N—CH$_2$—CH$_3$) and 7.0–9.0 (aromatic protons) respectively. LCMS gave peaks at M+ 325, 311, 268, 212, 127, 70. The product showed absorbance maxima at 578 nm in dichloromethane as a solvent and a Tg of 315° C.

Example 2

This example provides a general procedure for preparing a colored bisphenol A homopolycarbonate.

Extrusion: A 1 kilogram sample of bisphenol A homopolycarbonate and the benzopyran compound of Example 1 (0.02 weight percent of the overall sample), was placed in a polyethylene bag and shaken vigorously for about 3 to 4 minutes. The resulting material was then compounded under vacuum at the conditions specified in Table 1 to produce colored polymer pellets.

TABLE 1

| | |
|---|---|
| Feed zone temperature (° C.) | 128 |
| Zone 1 temperature (° C.) | 280 |
| Zone 2 temperature (° C.) | 285 |
| Zone 3 temperature (° C.) | 285 |
| Zone 4 temperature (° C.) | 290 |
| Throat/Die temperature (° C.) | 290 |
| Screw speed (Revolutions per minute) | 300 |
| Temperature of Melt (° C.) | 300 |
| Torque (Nm) | 58 to 62 |

Molding: The general procedure used for producing molded chips from the extruded pellets is as described below.

The extruded pellets prepared as described in the extrusion step were dried in an oven maintained at 120° C. for about 4 hours. Then the dried pellets were subjected to molding under the conditions shown in Table 2 below.

TABLE 2

| | |
|---|---|
| Feed zone temperature (° C.) | 110 |
| Zone 1 temperature (° C.) | 300 |
| Zone 2 temperature (° C.) | 290 |
| Zone 3 temperature (° C.) | 275 |
| Nozzle Temperature (° C.) | 295 |
| Temperature of Melt (° C.) | 300 |
| Mold temperature (° C.) | 85 |
| Sample drying time (hours) | 4 |
| Sample drying temperature (° C.) | 120 |
| Cycle time (seconds) | 125 |
| Injection time (seconds) | 1.2 |
| Injection speed (revolutions per minute) | 25 |
| Injection pressure (bar) | 50 |
| Screw speed (Revolutions per minute) | 300 |
| Holding pressure (bar) | 40 |
| Holding time (seconds) | 10 |
| Cooling time (seconds) | 15 |
| Thickness of step chip inserts (millimeters) | 1, 2, and 3 |
| Thickness of single insert (millimeters) | 2.54 |

Weatherability Testing: The molded chips incorporating the benzopyran compound as colorant were subjected to a weatherability test by using an Atlas Ci4000 weatherometer following ASTM D4459 test method (for indoor applications). The D65 illuminator was used since it most closely simulates natural sunlight. After being exposed for about 300 hours, the color of the sample was analyzed in the transmittance mode using a Macbeth Color Eye 7000A instrument equipped with an integrating sphere. The results are shown in Table 3. Sample measurements were made at exposure times of zero (control sample; before being placed in the Weatherometer), 100, 200, and 300 hours of exposure. The various parameters shown in Table 3 are: L Lightness; a*: redness-greenness, b*: yellowness-blueness; and C*: chroma; H*: hue; DL*: difference in lightness before and after exposure in weatherometer; Da*, Db*, and DC* represent the difference in difference in values for the a*, b*, and C*, respectively, before and after the exposure in weatherometer; DH*: difference in hue before and after exposure in weatherometer; and DE*, which represents the total color difference between the values obtained from before and after exposure in the weatherometer. DE* is derived from the Da*, Db*, and $\Delta L^*$ values, as shown in equation (1):

$$DE^* = [(DL^*)^2 + (Da^*)^2 + (Db^*)^2]^{1/2} \quad (1).$$

A negative DL indicates a darker sample relative to a control sample, while a positive DL indicates a relatively lighter sample. A negative Da* indicates a sample which is less red than the reference sample, while a positive Da* indicates that the sample is relatively more red. A negative Db* indicates a sample which is less yellow than the reference sample, while a positive Da* indicates that the sample is relatively more yellow. DC* is related to Da* and Db* by equation (2):

$$DC^* = [(Da^*)^2 + (Db^*)^2]^1 \quad (2)$$

TABLE 3

| Illumination Parameters Tested | 100 hours | 200 hours | 300 hours |
|---|---|---|---|
| L* | 68.385 | 68.338 | 67.441 |
| a* | 31.849 | 32.434 | 33.576 |
| b* | −34.717 | −33.899 | −34.565 |
| C* | 47.113 | 46.915 | 48.188 |
| h° | 312.533 | 313.735 | 314.168 |
| DL* | 0.812 | 2.178 | 2.447 |
| Da* | 0.244 | −0.972 | −1.715 |
| Db* | −1.460 | 0.074 | 0.867 |
| DC* | 1.234 | −0.73 | −1.82 |
| DH* | −0.818 | −0.646 | −0.615 |
| DE* | 1.689 | 2.386 | 3.111 |

The above results show that the colorants prepared as per Example 1 can be incorporated into polycarbonate as per Example 2. The colored polycarbonate so obtained provides good color value and also shows good weatherability properties as indicated in Table 3.

9,10,10-Trioxo-9,10-dihydro-1016-thioxanthene-3-carboxylic acid (6-cyano-9-diethylamino-7-oxa-4b,13-diazaindeno[2,1-a]anthracen-5-ylidene)-amide (Formula (I)) as prepared above in Example 1 was incorporated in polycarbonate by compounding polycarbonate powder using twin screw extruder and molded articles of 2.54 mm thickness obtained after subjecting pellets to molding using L& T Demag 60 molding machine. Molded plaques showed intense red fluorescence (Emission in Red region-590–610 nm) when exposed to 365 nm (long wavelength) UV irradiation with bright red edge glow effect. This indicates that the benzopyran colorants may also be used as fluorescent tags.

While typical embodiments have been set forth for the purpose of illustration, the foregoing descriptions should not be deemed to be a limitation on the scope herein. Accordingly, various modifications, adaptations, and alternatives may occur to one skilled in the art without departing from the spirit and scope herein.

The invention claimed is:

1. A compound of Formula (I)

(I)

[Chemical structure of Formula (I) with substituents X, $(R^1)_2N$, $(R^2)_n$, $(R^3)_m$, $(R^4)_p$, $(R^5)_q$, CN, O, and N]

wherein

X is hydrogen or a radical of Formula (II)

(II)

[Chemical structure of Formula (II) with substituents $(R^1)_2N$, $(R^2)_n$, $(R^3)_m$, CN, O, and N]

$R^1$ independently at each occurrence is a $C_1$–$C_{20}$ aliphatic radical, a $C_3$–$C_{10}$ cycloaliphatic radical, or a $C_3$–$C_{10}$ aromatic radical;

$R^2$, $R^3$, $R^4$ and $R^5$ are independently at each occurrence a halogen, a nitro group, a cyano group, a hydroxy group, a $C_1$–$C_{20}$ aliphatic radical, a $C_3$–$C_{20}$ cycloaliphatic radical, or a $C_6$–$C_{20}$ aromatic radical; and "n", "q", and "p" are each independently integers having a value of 0 to 3, and "m" is an integer having a value of 0 to 4.

2. A compound of claim 1, wherein $R^1$ independently at each occurrence is a $C_1$–$C_{10}$ aliphatic radical, a $C_3$–$C_{10}$ cycloaliphatic radical, or a $C_6$–$C_{10}$ aromatic radical.

3. A compound of claim 1, wherein each $R^1$ is the same, and is an unsubstituted $C_1$–$C_6$ aliphatic radical.

4. A compound of claim 1, wherein $R^2$, $R^3$, $R^4$ and $R^5$ are independently at each occurrence a halogen, a nitro group, or a cyano group; X is a radical of Formula (II); and "n", "q", "m" and "p" are each independently integers having a value of 0 to 2.

5. A compound of claim 1, wherein $R^2$, $R^3$, $R^4$ and $R^5$ are independently at each occurrence a halogen, a nitro group, or a cyano group; X is hydrogen; and "n", "q", "m" and "p" are each independently integers having a value of 0 to 2.

6. A compound of claim 1, wherein $R^2$ and $R^3$ are independently at each occurrence a halogen, a nitro group, or a cyano group; "n", "p", and "q" are each 0 or 1; and "m" is 0.

7. The compound of claim 1, wherein each $R^1$ is the same and is a $C_1$–$C_8$ aliphatic radical, X is hydrogen, and n, m, q, and p are each 0.

8. The compound of claim 1, wherein each $R^1$ is the same and is a $C_1$–$C_8$ aliphatic radical, X is a radical of Formula (II), and n, m, q, and p are each 0.

9. The compound of claim 1, wherein each $R^1$ is ethyl, n, m, q, and p are each 0.

10. A process comprising reacting a compound of Formula (III) with a compound of Formula V)

(III)

[Chemical structure of Formula (III) with $(R^1)_2N$, $(R^2)_n$, OH, and CHO]

(IV)

[Chemical structure of Formula (IV) with $(R^3)_m$, N, NH, and CN]

in the presence of a first catalyst and a first solvent to provide a compound of Formula (V)

[Chemical structure of Formula (V) with $(R^1)_2N$, $(R^2)_n$, $(R^3)_n$, O, NH, HN, and N]

reacting the compound of Formula (V) with malononitrile in the presence of a second solvent to provide a compound of Formula (VI)

(VI)

[Chemical structure of Formula (VI) with $(R^1)_2N$, $(R^2)_n$, $(R^3)_m$, CN, O, NH, and N]

reacting the compound of Formula (VI) with a compound of Formula (VII) or Formula (VIII)

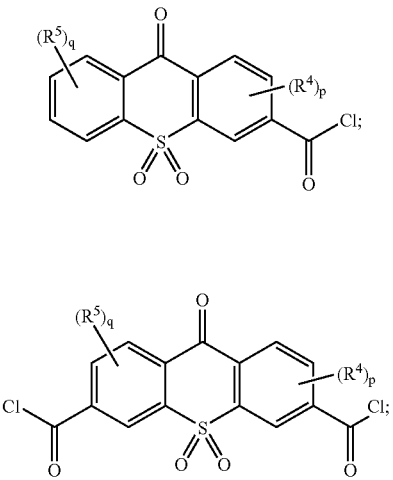

in the presence of a second catalyst and a third solvent to provide a compound of Formula (I)

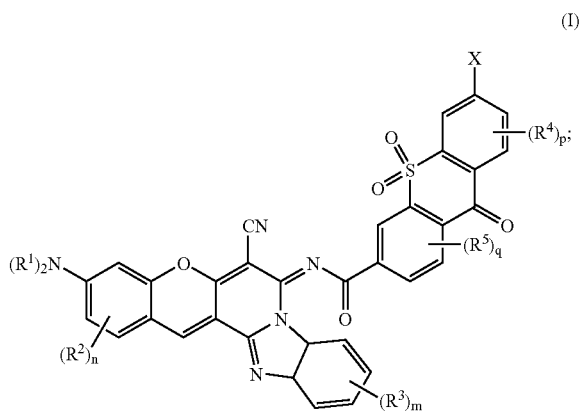

wherein
X is hydrogen or a radical of the Formula (II);

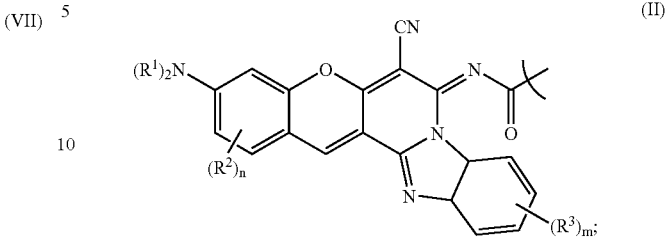

$R^1$ independently at each occurrence is a $C_1$–$C_{20}$ aliphatic radical, a $C_3$–$C_{10}$ cycloaliphatic radical, or a $C_3$–$C_{10}$ aromatic radical;

$R^2$, $R^3$, $R^4$ and $R^5$ are independently at each occurrence a halogen, a nitro group, a cyano group, a hydroxy group, a $C_1$–$C_{20}$ aliphatic radical, a $C_3$–$C_{20}$ cycloaliphatic radical, or a $C_6$–$C_{20}$ aromatic radical; and "n", "p", and "q" are each independently integers having a value of 0 to 3, "m" is an integer having a value of 0 to 4.

11. The process of claim 10, wherein $R^1$ is ethyl and m, n, o, and p are each 0; the first catalyst is piperidine and the first solvent is methanol, the second solvent is ethyl cellosolve, and the third solvent is pyridine.

12. The process of claim 10 where the compound of Formula (III) is 4-diethylamino-2-hydroxybenzaldehyde.

13. The process of claim 10 where the compound of Formula (IV) is 2-(cyanomethyl)benzimidazole.

14. The process of claim 10 where the compound of Formula (VII) is 9-oxo-9H-thioxanthene-10,10-dioxide-3-carboxylic acid chloride.

15. The process of claim 10 where the compound of Formula (I) is 9,10,10-trioxo-9,10-dihydro-10,16-thioxanthene-3-carboxylic acid (6-cyano-9-diethylamino-7-oxa-4b,13-diaza-indeno[2,1-a]anthracen-5-ylidene)-amide.

16. A composition comprising the compound of claim 1 and a thermoplastic resin.

17. The composition of claim 16, wherein the compound of Formula (I) is present in an amount of about 0.05 to about 20 percent by weight, based on the weight of the thermoplastic resin.

* * * * *